(12) United States Patent
Lee et al.

(10) Patent No.: US 7,186,508 B2
(45) Date of Patent: Mar. 6, 2007

(54) CAPTURE AND DETECTION OF TARGET NUCLEIC ACID IN DIPSTICK ASSAYS

(75) Inventors: Helen Lee, Cambridge (GB); Magda Anastassova Dineva, Cambridge (GB); Shaun Christopher Hazlewood, Suffolk (GB)

(73) Assignee: Diagnostics for the Real World, Ltd., Sunnyvale, CA (US)

( * ) Notice: Subject to any disclaimer, the term of this patent is extended or adjusted under 35 U.S.C. 154(b) by 286 days.

(21) Appl. No.: 10/332,134

(22) PCT Filed: Jul. 6, 2001

(86) PCT No.: PCT/GB01/03024

§ 371 (c)(1),
(2), (4) Date: Apr. 7, 2003

(87) PCT Pub. No.: WO02/04668

PCT Pub. Date: Jan. 17, 2002

(65) Prior Publication Data

US 2006/0094005 A1    May 4, 2006

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .................. 435/6; 536/23.1, 24.3
See application file for complete search history.

(56) References Cited

U.S. PATENT DOCUMENTS

| | | | |
|---|---|---|---|
| 4,358,535 A | 11/1982 | Falkow et al. | 435/5 |
| 5,030,557 A | 7/1991 | Hogan et al. | 435/6 |
| 5,310,650 A * | 5/1994 | McMahon et al. | 435/6 |
| 5,969,122 A | 10/1999 | Hammond et al. | 536/23.1 |
| 6,821,770 B1 * | 11/2004 | Hogan | 435/287.2 |
| 2002/0197614 A1 * | 12/2002 | Weir et al. | 435/6 |

FOREIGN PATENT DOCUMENTS

| | | |
|---|---|---|
| CA | 1215904 | 12/1986 |
| EP | 0318245 | 5/1989 |
| EP | 0336412 | 10/1989 |
| EP | 0499681 | 8/1992 |
| WO | WO84/02721 | 7/1984 |
| WO | WO94/29696 | 12/1994 |
| WO | WO95/27081 | 10/1995 |
| WO | WO96/12040 | 4/1996 |
| WO | WO00/09756 | 2/2000 |

OTHER PUBLICATIONS

Sriprakash et al. PLASMID 18(3): 205-214 (1987).

* cited by examiner

*Primary Examiner*—Ethan Whisenant
(74) *Attorney, Agent, or Firm*—Proskauer Rose LLP

(57) ABSTRACT

Use of helper probes in dipstick assays is described. In a dipstick assay to test for the presence of a target nucleic acid in a sample solution, the sample solution is connected with the contact end of the dipstick to cause the sample solution is contacted with the contact end of the dipstick to cause the sample solution to move by capillary action to a capture zone of the dipstick at which target nucleic acid is captured. The target nucleic acid may be captured at the capture zone by a capture probe capable of hybridising to the target nucleic acid. A labelled detection probe capable of hybridising to the target nucleic acid may be used to detect the target nucleic acid at the capture zone. A helper probe may be used to enhance the binding of the capture and/or detection probe to the target nucleic acid, thereby improving the sensitivity of target nucleic acid detection. Dipsticks and kits are also described.

35 Claims, 8 Drawing Sheets

Figure 2

HP SEQ ID No 1: 5' GAT AAA ATC CCT TTA CCC ATG AAA
HP SEQ ID No 1: 5' CTT GCT GCA AAG ATA AAA TCC CTT
HP SEQ ID No 2: 5' TAA AAT GTC CTG ATT AGT GAA ATA AT
HP SEQ ID No 3: 5' TCG GTA TTT TTT TAT ATA AAC ATG AAA A
HP SEQ ID No 4: 5' TGC AAG ATA TCG AGT ATG CGT TGT TA
HP SEQ ID No 5: 5' AAA GGG AAA ACT CTT GCA GA
HP SEQ ID No 6: 5' TCT TTT CTA AAG ACA AAA AAG ATC CTC GAT

SEQ ID No 7: 5' CTT GCT GCT CGA ACT TGT TTA GTA C
SEQ ID No 8: 5' AGA AGT CTT GGC AGA GGA AAC TTT T
SEQ ID No 9: 5' CTA GAA TTA GAT TAT GAT TTA AAA GGG
SEQ ID No 10: 5' TTC ATA TCC AAG GAC AAT AGA CCA A
SEQ ID No 11: 5' TGA TCT ACA AGT ATG TTT GTT GAG T
SEQ ID No 12: 5' TGC ATA ATA ACT TCG AAT AAG GAG AAG
SEQ ID No 13: 5' TCC CTC GTG ATA TAA CCT ATC CG
SEQ ID No 14: 5' CAG GTT GTT AAC AGG ATA GCA CGC
SEQ ID No 15: 5' CTC GTT CCG AAA TAG AAA ATC GCA
SEQ ID No 16: 5' GGT AAA GCT CTG ATA TTT GAA GAC
SEQ ID No 17: 5' CTG AGG CAG CTT GCT AAT TAT GAG T
SEQ ID No 18: 5' GTT GGG AAA AAT AGA CAT GGA TCG G

Figure 10

| No EB* | 5x10⁶ | 10⁶ | 5x10⁵ | 2.5x10⁵ | 10⁵ | 7.5x10⁴ | 5x10⁴ | 2.5x10⁴ | 10⁴ | 5x10³ | NC** |
|---|---|---|---|---|---|---|---|---|---|---|---|
| Time first signal | 2.20' | 2.50' | 3.30' | 4.30' | 5.35' | 8.10' | 8.45' | 14.05' | 24' | - | - |
| Signal at 10' | 4 | 3 | 2.5 | 2 | 1.5 | 1 | 1 | 0.5 | 0 | 0 | 0 |
| Signal at 20' | 5 | 4 | 3.5 | 3 | 2.5 | 2 | 1.5 | 1 | 0.25 | 0 | 0 |
| Signal at 30' | 5 | 4.5 | 4.0 | 3.5 | 3.0 | 2.5 | 2.0 | 1.5 | 1.0 | 0 | 0 |
| Signal at 1 h | 5 | 4.5 | 4.0 | 3.5 | 3.0 | 2.5 | 2.0 | 1.0 | 0.5 | 0 | 0 |

*Number elementary bodies (EB) of *Chlamydia trachomatis*
**NC: Negative control

|  | A) Ab Capture | B) Direct Probe Capture | C) Universal Probe Capture |
|---|---|---|---|
| Signal 5xE9 | 3.5 | 2.0 | 3.0 |
| Sensitivity | E9 | 5xE9 | E9 |
|  | D) Ab Capture – with helper probes | E) Direct Probe Capture – with helper probes | F) Universal Probe Capture – with helper probes |
| Signal 5xE9 | 3.5 | 4.0 | 3.0 |
| Sensitivity | E9 | 5xE8 | 5xE8 (very faint) |

CAPTURE AND DETECTION OF TARGET NUCLEIC ACID IN DIPSTICK ASSAYS

The present invention relates to methods for improved detection of nucleic acid by dipsticks. Methods of the invention are used to test for the presence of a target nucleic acid in a sample solution, for example to identify whether a patient is infected with a disease causing microorganism such as *Chlamydia trachomatis* (CT).

Some conventional methods for testing for the presence of a target nucleic acid in a sample solution rely on amplification of the target nucleic acid using the polymerase chain reaction (PCR). Whilst this reaction allows detection of small quantities of target nucleic acid, it can is take several hours before a result is obtained. This can be a significant disadvantage because it is often desired to obtain the result as soon as possible, for example, to keep patient waiting times to a minimum. Further disadvantages of such methods are the requirement for expensive specialist equipment to perform the reaction and the relatively high cost of the reagents.

In contrast, dipsticks can detect unamplified target nucleic acid without the requirement for any specialist equipment. The results can be obtained much more rapidly than PCR-based methods and, therefore, in a single visit from a patient. The patient can then be treated in the same visit. This is particularly advantageous where the patient is unlikely to, or cannot return for treatment at a later date. The cost of performing a dipstick test can also be significantly lower than the cost of a PCR-based test.

In a typical, conventional dipstick described in U.S. Pat. No. 5,310,650, a single stranded DNA capture probe is immobilised on a nitrocellulose filter at a capture zone remote from one end of the filter (the contact end). The sequence of the capture probe is complementary to the sequence of a first region of the target nucleic acid to be detected. A labelled single stranded DNA detection probe is releasably immobilised on the nitrocellulose filter at a probe zone located between the capture zone and the contact end of the filter. The sequence of the detection probe is complementary to the sequence of a second region (distinct from the first region) of the target nucleic acid.

To detect target DNA in a sample solution thought to contain target DNA, the contact end of the nitrocellulose filter is contacted with the sample solution. The sample solution wicks up the filter by capillary action and passes the probe zone and the capture zone. As the sample solution passes the probe zone, it mobilises the detection probe and causes it to rise with the sample solution towards the capture zone. Mobilised detection probe can then hybridise to the second region of any target DNA present in the sample solution. When the hybridised detection probe and target DNA arrive at the capture zone, the first region of the target DNA can hybridise to the immobilised capture probe. A ternary complex is thereby formed between the target nucleic acid, the capture probe and the labelled detection probe. Presence of label at the capture zone, therefore, indicates that target DNA is present in the sample solution.

With a second type of conventional dipstick, the labelled DNA detection probe is not immobilised on the nitrocellulose filter. Instead the detection probe is added to the sample solution under conditions allowing hybridisation of the detection probe to any target nucleic acid in the sample solution. The contact end of the nitrocellulose filter is then contacted with the sample solution and as the sample solution wicks up the dipstick, target nucleic acid which is hybridised to the detection probe rises up the nitrocellulose filter and may be captured at the capture zone by the capture probe.

Although results can be obtained more rapidly using conventional dipsticks than detection methods which require amplification of the target nucleic acid, the sensitivity of nucleic acid detection by conventional dipsticks can be low. The sensitivity of detection of double stranded target nucleic acid by conventional dipsticks can be particularly low especially as the size of the target nucleic acid increases, and circular double stranded target nucleic acid is thought to be virtually undetectable using conventional dipsticks. Consequently, the presence of target nucleic acid in a sample solution can sometimes be undetected. It is desired, therefore, to improve the sensitivity of target nucleic acid detection, in particular the sensitivity of double stranded and circular double stranded target nucleic acid detection by dipsticks.

In its broadest sense, the invention provides use of a helper probe in a dipstick assay to enhance the hybridisation of a capture and/or detection probe to the target nucleic acid.

The term "dipstick assay" as used herein means any assay using a dipstick in which sample solution is contacted with the dipstick to cause sample solution to move by capillary action to a capture zone of the dipstick thereby allowing target nucleic acid in the sample solution to be captured and detected at the capture zone.

According to a first aspect of the invention there is provided a method for testing for the presence of target nucleic acid in a sample solution which comprises:

a) providing a chromatographic strip having: a contact end for contacting the sample solution; and a capture probe immobilised at a capture zone of the chromatographic strip remote from the contact end, the capture probe being capable of hybridising to a first sequence of the target nucleic acid;

b) incubating the sample solution with a detection probe capable of attaching to the target nucleic acid under conditions for attachment of the detection probe to target nucleic acid, thereby allowing direct or indirect detection of target nucleic acid utilising the detection probe; and a first helper probe capable of hybridising to a second sequence of the target nucleic acid and thereby enhancing hybridisation of the capture probe to target nucleic acid, the sample solution and the first helper probe being incubated under conditions for hybridisation of the first helper probe to target nucleic acid;

c) contacting the contact end of the chromatographic strip with the sample solution so that a complex formed between the detection probe, the first helper probe and target nucleic acid can move by capillary action to the capture zone and bind to the capture zone by hybridisation of the capture probe to target nucleic acid of the complex; and d) checking for the presence of detection probe at the capture zone.

There is also provided according to the first aspect of the invention a kit for testing for the presence of target nucleic acid in a sample solution suspected of containing target nucleic acid which comprises:

i) a dipstick comprising:
a chromatographic strip having a contact end for contacting the sample solution; and
a capture probe immobilised at a capture zone of the chromatographic strip remote from the contact end, the capture probe being capable of hybridising to a first sequence of the target nucleic acid;

ii) a first helper probe capable of hybridising to a second sequence of the target nucleic acid and thereby enhancing hybridisation of the capture probe to the target nucleic acid; and optionally iii) a detection probe capable of attaching to target nucleic acid to allow direct or indirect detection of the target nucleic acid utilising the detection probe.

The term "chromatographic strip" used herein means any porous strip of material capable of transporting a solution by capillarity.

The detection probe and the first helper probe may be incubated with the sample solution in any order or they may be added at the same time to the sample solution.

It will be understood that the contact end of the chromatographic strip will normally be contacted with the sample solution after the sample solution has been incubated with the detection probe and the first helper probe according to step (b). However, it is not essential for the working of the invention that the contact end is contacted with the sample solution after step (b) has been completed—the contact end of the chromatographic strip may be contacted with the sample solution before or during step (b).

The capture probe of the first aspect of the invention may comprise a single probe, or more than one probe. For example the capture probe may comprise a universal capture probe immobilised to the chromatographic strip and a hook capture probe hybridised to the universal capture probe, the hook probe being capable of hybridising to the first sequence of the target nucleic acid.

An advantage of using a universal probe and a hook probe as the capture probe is that chromatographic strips which have the universal probe immobilised to them may be used to detect any target nucleic acid. A hook probe capable of hybridising to the desired target nucleic acid is simply selected and hybridised to the universal probe before the chromatographic strip is used to test for the presence of the desired target nucleic acid.

According to a second aspect of the invention there is provided a method for testing for the presence of target nucleic acid in a sample solution which comprises:

a) providing a chromatographic strip having: a contact end for contacting the sample solution; and a capture moiety immobilised at a capture zone of the chromatographic strip remote from the contact end;

b) incubating the sample solution with:

a detection probe capable of attaching to the target nucleic acid under conditions for attachment of the detection probe to target nucleic acid, thereby allowing direct or indirect detection of target nucleic acid utilising the detection probe;

a capture probe capable of hybridising to a first sequence of the target nucleic acid under conditions for hybridisation of the capture probe to the first sequence, the capture probe being capable of being bound by the capture moiety when the capture probe has hybridised to the first sequence; and a first helper probe capable of hybridising to a second sequence of the target nucleic acid and thereby enhancing hybridisation of the capture probe to target nucleic acid, the sample solution and the first helper probe being incubated under conditions for hybridisation of the first helper probe to the second sequence;

c) contacting the contact end of the chromatographic strip with the sample solution so that a complex formed between the detection probe, the capture probe, the first helper probe and target nucleic acid can move by capillary action to the capture zone and bind to the capture zone by binding of the capture moiety to the capture probe of the complex; and d) checking for the presence of detection probe at the capture zone.

According to the second aspect of the invention there is also provided a kit for testing for the presence of a target nucleic acid in a sample solution which comprises:

i) a dipstick comprising:

a chromatographic strip having a contact end for contacting the sample solution; and a capture moiety immobilised at a capture zone of the chromatographic strip remote from the contact end;

ii) a capture probe capable of hybridising to a first sequence of the target nucleic acid and which can be bound by the capture moiety when the capture probe has hybridised to the first sequence;

iii) a first helper probe capable of hybridising to a second sequence of the target nucleic acid and thereby enhancing hybridisation of the capture probe to the first sequence; and optionally iii) a detection probe capable of attaching to the target nucleic acid to allow direct or indirect detection of the target nucleic acid.

The capture moiety of the second aspect of the invention may comprise a universal capture probe capable of hybridising to the capture probe. Alternatively the capture moiety may be capable of binding by non base pairing interaction to the capture probe once the capture probe has hybridised to the target nucleic acid.

For example, the capture moiety may comprise an antibody or antibody fragment capable of binding to the duplex formed when the capture probe has hybridised to the target nucleic acid. Alternatively, the capture probe may comprise a capture ligand which can be bound by the capture moiety. When the capture probe comprises a capture ligand the capture moiety may comprise an antibody or antibody fragment. If the capture ligand comprises biotin the capture moiety may comprise an anti-biotin antibody or streptavidin, avidin, or a derivative thereof which retains biotin binding activity.

The second sequence of the first and second aspects of the invention should be in a different region of the target nucleic acid to the first sequence. Preferably the second sequence is spaced up to 10 nucleotides from the first sequence. More preferably the second sequence is immediately adjacent the first sequence.

In preferred methods of the first and second aspects of the invention the sample solution is incubated with a second helper probe capable of hybridising to a third sequence of the target nucleic acid and thereby enhancing hybridisation of the capture probe to target nucleic acid, the sample solution and the second helper probe being incubated under conditions for hybridisation of the second helper probe to target nucleic acid.

The third sequence should be in a different region of the target nucleic acid to the first and second sequences. Preferably the second and third sequences flank the first sequence. More preferably the second and third sequences are spaced up to 10 nucleotides each side of the first sequence. Most preferably the second and third sequence are immediately adjacent each side of the first sequence.

The capture probe, detection probe and helper probes may comprise nucleic acids or nucleic acid analogues. The capture probe may comprise a single probe, or more than one probe.

The detection probe of the first and second aspects of the invention may be a label which covalently attaches to the target nucleic acid thereby allowing direct detection of target nucleic acid. Alternatively the detection probe may be a ligand which covalently attaches to the target nucleic acid thereby allowing indirect detection of target nucleic acid using a ligand binding moiety capable of binding to the ligand. The detection probe may be added to the sample solution in the form of a precursor which reacts with the target nucleic acid to covalently attach the detection probe to the target nucleic acid.

Alternatively, the detection probe may be capable of attaching to the target nucleic acid by non covalent interaction. For example, the detection probe may be capable of hybridising to a fourth sequence of the target nucleic acid. The detection probe may be labelled thereby allowing direct detection of the target nucleic acid when the detection probe has attached to the target nucleic acid by non covalent interaction. Alternatively, the detection probe may comprise a ligand thereby allowing indirect detection of the target nucleic acid using a ligand binding moiety when the detection probe has attached to the target nucleic acid by non covalent interaction.

Preferred labels are non radioactive labels. Examples of suitable labels include textile dyes, metal sol such as colloidal gold and coloured particles such as coloured latex particles. Examples of suitable ligands include biotin (detectable for example by an anti-biotin antibody, or by streptavidin or avidin or a derivative thereof which retains biotin binding activity), fluorescein (detectable for example by an anti-fluorescein antibody), and 2,4-dinitrophenol (DNP) (detectable for example by an anti-DNP antibody).

Further improved sensitivity of detection of target nucleic acid may be obtained if the sample solution is incubated with a third and, preferably, also with a fourth helper probe. The third helper probe is capable of hybridising to a fifth sequence of the target nucleic acid and the fourth helper probe is capable of hybridising to a sixth sequence of the target nucleic acid, thereby enhancing hybridisation of the detection probe to the fourth sequence. The sample solution and the third and fourth helper probes are incubated under conditions for hybridisation of the third and fourth helper probes to target nucleic acid.

It is possible that any significant enhancement of the sensitivity of detection using the third and fourth helper probes may only be observed when the first and the fourth sequences of the target nucleic acid are at least 200 nucleotides apart.

Preferably the fifth and sixth sequences flank the fourth sequence. More preferably the fifth and sixth sequences are spaced up to lo nucleotides each side of the fourth sequence. Most preferably the fifth and sixth sequences are immediately adjacent each side of the fourth sequence.

According to a third aspect of the invention there is provided a method for testing for the presence of target nucleic acid in a sample solution which comprises:
a) providing a chromatographic strip having: a contact end for contacting the sample solution; and a capture probe immobilised at a capture zone of the chromatographic strip remote from the contact end, the capture probe being capable of hybridising to a first sequence of the target nucleic acid;
b) incubating the sample solution with:
a detection probe capable of hybridising to a second hybridisation of the detection probe to target nucleic acid, thereby allowing direct or indirect detection of target nucleic acid utilising the detection probe; and
a first helper probe capable of hybridising to a third sequence of the target nucleic acid and thereby enhancing hybridisation of the detection probe to the second sequence, the sample solution and the first helper probe being incubated under conditions for hybridisation of the first helper probe to the third sequence;
c) contacting the contact end of the chromatographic strip with the sample solution so that a complex formed between the detection probe, the first helper probe and target nucleic acid can move by capillary action to the capture zone and bind to the capture zone by hybridisation of the capture probe to the target nucleic acid of the complex; and
d) checking for the presence of detection probe at the capture zone.

According to the third aspect of the invention there is also provided a kit for testing for the presence of a target nucleic acid in a sample solution suspected of containing target nucleic acid which comprises:
i) a dipstick comprising:
a chromatographic strip having a contact end for contacting the sample solution; and a capture probe immobilised at a capture zone of the chromatographic strip remote from the contact end, the capture probe being capable of hybridising to a first sequence of the target nucleic acid;
ii) a detection probe capable of hybridising to a second sequence of the target nucleic acid to allow direct or indirect detection of the target nucleic acid; and
iii) a first helper probe capable of hybridising to a third sequence of the target nucleic acid and thereby enhancing hybridisation of the detection probe to the second sequence.

The capture probe of the third aspect of the invention may comprise a single probe, or more than one probe. For example the capture probe may comprise a universal capture probe immobilised to the chromatographic strip and a hook capture probe hybridised to the universal capture probe, the hook probe being capable of hybridising to the first sequence of the target nucleic acid.

According to a fourth aspect of the invention there is provided a method for testing for the presence of target nucleic acid in a sample solution which comprises:
a) providing a chromatographic strip having: a contact end for contacting the sample solution; and a capture moiety immobilised at a capture zone of the chromatographic strip remote from the contact end;
b) incubating the sample solution with:
a capture probe capable of hybridising to a first sequence of the target nucleic acid under conditions for hybridisation of the capture probe to the first sequence, the capture probe being capable of being bound by the capture moiety when the capture probe has hybridised to the first sequence;
a detection probe capable of hybridising to a second sequence of the target nucleic acid under conditions for hybridisation of the detection probe to the second sequence, thereby allowing direct or indirect detection of target nucleic acid utilising the detection probe; and
a first helper probe capable of hybridising to a third sequence of the target nucleic acid and thereby enhancing hybridisation of the detection probe to target nucleic acid, the sample solution and the first helper probe being incubated under conditions for hybridisation of the first helper probe to the third sequence;
c) contacting the contact end of the chromatographic strip with the sample solution so that a complex formed between the detection probe, the capture probe, the first helper probe and target nucleic acid can move by capillary action to the capture zone and bind to the capture zone by binding of the capture moiety to the capture probe of the complex; and d) checking for the presence of detection probe at the capture zone.

According to the fourth aspect of the invention there is also provided a kit for testing for the presence of a target nucleic acid in a sample solution suspected of containing target nucleic acid which comprises:

i) a dipstick comprising:
a chromatographic strip having a contact end for contacting the sample solution; and a capture moiety immobilised at a capture zone of the chromatographic strip remote from the contact end;

ii) a capture probe capable of hybridising to a first sequence of the target nucleic acid and which can be bound by the capture moiety when the capture probe has hybridised to the first sequence;

iii) a detection probe capable of hybridising to a second sequence of the target nucleic acid to allow direct or indirect detection of the target nucleic acid; and iv) a first helper probe capable of hybridising to a third sequence of the target nucleic acid and thereby enhancing hybridisation of the detection probe to the second sequence.

The capture moiety of the fourth aspect of the invention may comprise a universal capture probe capable of hybridising to the capture probe. Alternatively the capture moiety may be capable of binding by non base pairing interaction to the capture probe once the capture probe has hybridised to the target nucleic acid.

For example, the capture moiety may comprise an antibody or antibody fragment capable of binding to the duplex formed when the capture probe has hybridised to the target nucleic acid. Alternatively, the capture probe may comprise a capture ligand which can be bound by the capture moiety. When the capture probe comprises a capture ligand the capture moiety may comprise an antibody or antibody fragment. If the capture ligand comprises biotin the capture moiety may comprise an anti-biotin antibody or streptavidin, avidin, or a derivative thereof which retains biotin binding activity.

The detection probe of the third and fourth aspects of the invention may be labelled thereby allowing direct detection of the target nucleic acid when the detection probe has hybridised to the target nucleic acid. Alternatively, the detection probe may comprise a ligand thereby allowing indirect detection of the target nucleic acid using a ligand binding moiety when the detection probe has hybridised to the target nucleic acid.

The third sequence in methods of the third and fourth aspect of the invention is preferably spaced up to 10 nucleotides from the second sequence. More preferably the third sequence is immediately adjacent the second sequence.

Preferably in methods of the third and fourth aspects of the invention the sample solution is incubated with a second helper probe capable of hybridising to a fourth sequence of the target nucleic acid and thereby enhancing hybridisation of the detection probe to target nucleic acid, the sample solution and the second helper probe being incubated under conditions for hybridisation of the second helper probe to the fourth sequence.

Preferably with methods of the third and fourth aspects of the invention the third and fourth sequences flank the second sequence. More preferably the fourth sequence is spaced up to 10 nucleotides from the second sequence. Most preferably the fourth sequence is immediately adjacent the second sequence.

It is possible that any significant enhancement of the sensitivity of detection using the first and second helper probes in methods of the third and fourth aspects of the invention may only be observed when the first and the second sequences of the target nucleic acid are at least 200 nucleotides apart.

If the detection probe of a kit of the invention comprises a detection ligand, the kit may further comprise a labelled detection ligand binding moiety capable of binding to the detection ligand thereby enabling detection of target nucleic acid utilising the detection probe and the detection ligand binding moiety. The detection ligand binding moiety may be an antibody, an antibody fragment or a non antibody.

Kits of the invention may further comprise any reagent required to allow detection of target nucleic acid in the sample solution utilising the chromatographic strip.

There is also provided according to the invention a substantially isolated nucleic acid molecule or nucleic acid analogue having a sequence corresponding to the sequence of any of SEQ ID NOS: 1–18.

There is also provided according to the invention use of a substantially isolated nucleic acid molecule or nucleic acid analogue of the invention as a helper probe to enhance detection of CT target nucleic acid in a test for the presence of such target nucleic acid in a sample solution.

The helper probes used in methods of the invention may enhance the binding of capture or detection probes to single stranded or double stranded target nucleic acid. Where the target nucleic acid is single stranded, it is thought that the helper probe may enhance the binding of the capture/detection probe to the target nucleic acid by ensuring that the target nucleic acid does not form significant secondary structure in the region of the target nucleic acid to which the capture/detection probe binds.

It will be appreciated that the region of the target nucleic acid to which the helper probe binds may not always be close to or immediately adjacent the region to which the capture/detection probe binds. Hybridisation of a helper probe to one region of target nucleic acid could alter its secondary structure at a remote location, thereby allowing a capture/detection probe to bind more easily to the target nucleic acid at that remote location.

Consequently, the region of the target nucleic acid to which the helper probe binds is likely to differ depending on the identity of the target nucleic acid and of the capture/detection probe. However, a person skilled in the art can readily determine which helper probes are most effective by experimenting with different probes and different lengths of probe.

Where the target nucleic acid is double stranded, it is thought that hybridisation of a helper probe to the target nucleic acid enhances hybridisation of the capture or detection probe to the target nucleic acid by opening up the double strands of the target nucleic acid in the region in which the capture or detection probe binds. Consequently, for double stranded target nucleic acid, it will normally be expected that a helper probe binds adjacent the region to which the capture or detection probe binds.

In order for a helper probe to enhance the binding of a capture or detection probe to the target nucleic acid, the helper probe should be hybridised to the target nucleic acid before or at the same time as the capture or detection probe is hybiridised to the target nucleic acid, but not after the capture or detection probe has been hybridised to the target nucleic acid.

In some embodiments, a helper probe may enhance the hybridisation of a capture and a detection probe to the target nucleic acid. This may be achieved, for example, if the helper probe hybridises to a region of the target nucleic acid between the capture and detection probes.

In other embodiments of the invention, one or more of the probes may be releasably immobilised to the chromatographic strip, between the contact end and the capture zone, in such a way that movement of the sample solution from the contact end to the capture zone by capillary action will cause the or each probe to be released from the chromatographic strip into the sample solution. Released probe can then hybridise to target nucleic acid in the sample solution.

For embodiments of the invention in which a helper probe is provided which is capable of enhancing hybridisation of a detection probe to the target nucleic acid, the helper probe (preferably with the detection probe) may be contacted with the capture zone of the chromatographic strip after the sample solution has been contacted with the contact end of the chromatographic strip to allow capture of target nucleic acid at the capture zone. This may be achieved by applying a separate helper probe solution containing the helper probe (and detection probe) directly to the capture zone, or by contacting the contact end of the chromatographic strip with the helper probe solution after the sample solution, thereby causing the helper probe to move by capillary action to the capture zone. If the detection probe is not in the helper probe solution, this will need to be contacted with the capture zone after the helper probe.

However, in preferred methods of the invention, hybridisation of the probes to target nucleic acid (other than where a capture probe is immobilised at the capture zone) is carried out in the sample solution before the sample solution is contacted with the chromatographic strip. Most preferably hybridisation of the probes is carried out in a single step. This simplifies the methods, thereby making them considerably quicker and easier to perform.

Multiple step hybridisation may be carried out by sequential hybridisation of the different probes to the target nucleic acid in the sample solution, or by contacting the dipstick with different solutions each containing a different probe. Usually, the latter method of multiple step hybridisation will involve washing the dipstick between each contact with a different probe solution.

Whilst there may be circumstances in which multiple step hybridisation is preferred, it will be appreciated that the simpler and quicker format of one step hybridisation will usually be preferred.

It is most preferred that the sample solution is of suitable is composition to allow the hybridisation reactions to take place in a single hybridisation step and also to allow non base pairing interactions to take place (for example between a detection ligand and a detection ligand binding moiety and between a capture ligand and a capture ligand binding moiety) and transport a complex comprising target nucleic acid and one or more hybridised probes and (optionally) ligand binding moieties by capillary action up the dipstick.

Using such a sample solution, it will be appreciated that the hybridisation reactions can then be carried out in a single step, and any ligand-ligand binding moiety interactions can take place, before the sample solution is contacted directly with the contact end of the dipstick (without the need to first dilute or alter the sample solution). Ligand-ligand binding moiety interactions can additionally or alternatively take place on the dipstick if desired as the sample solution travels to the capture zone. Simple and rapid dipstick detection of target nucleic acid is thereby facilitated.

We have found that such results are achieved with sample solutions comprising a standard hybridisation buffer (such as SSPE buffer or Tris buffer) with salt, detergent and a blocking protein such as BSA or powdered milk. The sensitivity of detection of target nucleic acid using such assays has been found to be about equal to or better than that of other dipstick assays.

Embodiments of the invention are now described by way of example with reference to the accompanying drawings in which:

FIG. 1 shows a dipstick used to detect target nucleic actd in accordance with an embodiment of the invention;

FIG. 2 lists the sequences of help probes (SEQ ID NOS 1, 19 and 2–18, respectively, in order of appearance) which can be used in accordance with the invention;

FIG. 10 shows the results of a one-step nucleic acid dipstick assay detection of *Clamydia trachomatis*.

Figure 1:
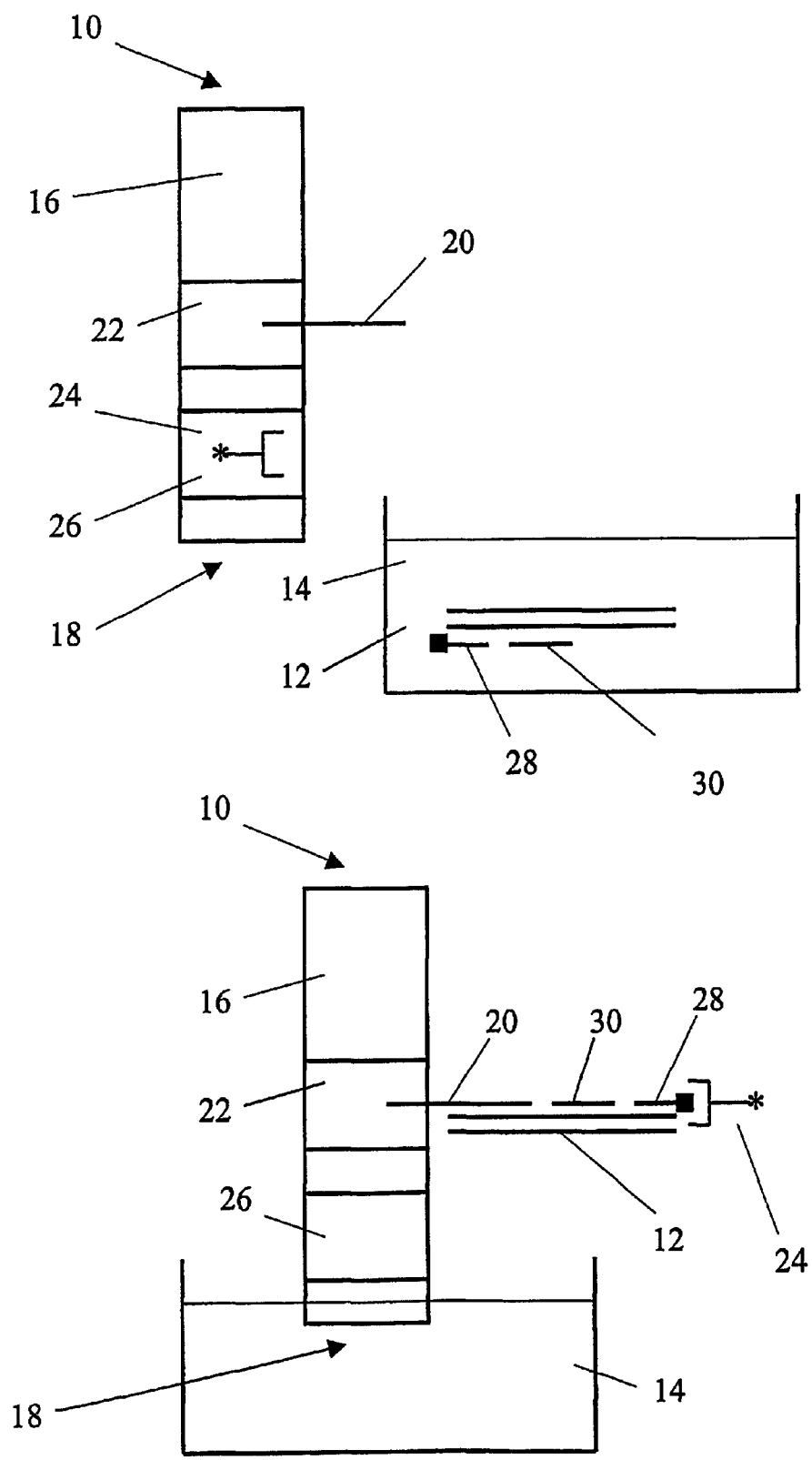
Figure 3:
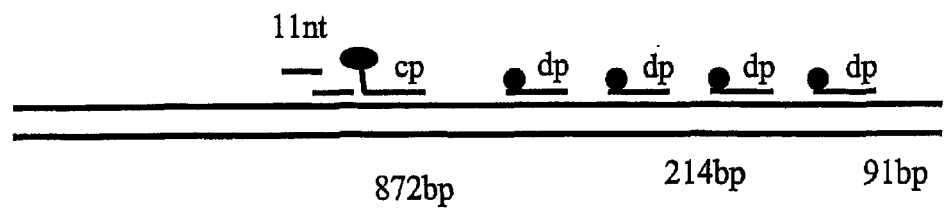
FIG. 3 shows the experimental set for Example 1.

The following examples illustrate improved sensitivity of detection of target nucleic acid using methods of the invention. The examples relate to detection of a DNA fragment of the cryptic plasmid of *Chlamydia trachomatis* (CT).

CT is one of the most common causes of sexually transmitted disease. CT infections can cause infertility and, during pregnancy, can result in spontaneous abortion, still birth or postpartum endometritis. In neonates, CT infection can cause blindness and chronic respiratory disease. Approximately 10% of infected men and upto 70% of infected women do not show symptoms of CT infection. Consequently, accurate diagnosis of CT infection is important so that early treatment of the disease can be initiated.

In the following examples a dipstick 10 is used to try to detect double stranded CT target nucleic acid 12 in a sample solution 14. The dipstick 10 comprises a strip of nitrocellulose 16 having a contact end 18 for contacting the sample solution 14 and a capture probe 20 immobilised at a capture zone 22 of the nitrocellulose strip 16 remote from the contact end 18. An anti-biotin antibody-dye conjugate 24 is releasably immobilised at a conjugate zone 26 of the nitrocellulose strip located between the contact end 18 and the capture zone 22. The capture probe 20 is capable of hybridising to a first sequence of one strand (the first strand) of the target nucleic acid 12.

A detection probe 28 and a helper probe 30 each capable of hybridising to distinct regions of the first strand of the double stranded target nucleic acid 12 are then added to the sample solution 14. The detection probe 28 comprises a nucleic acid coupled to biotin (using methods well known to those of skill in the art). The sample solution 14 containing the detection probe 28 and the helper probe 30 is then heated to a temperature sufficient to separate the complementary strands of the double stranded target nucleic acid 12 from each other at least in the region of the first strand to which the detection probe 28 and helper probe 30 bind, and then cooled to allow hybridisation of the detection probe 28 and the helper probe 30 to the first strand of the double stranded target nucleic acid. As the detection probe and helper probe hybridise to the first strand, the second strand re-anneals to the first strand, but is prevented from re-annealing to the region of the first strand which is bound by the detection probe 28 and the helper probe 30.

The contact end 18 of the dipstick 10 is then contacted with the sample solution 14. The sample solution 14 and any target nucleic acid 12 hybridised to the detection probe 28 and the helper probe 30 moves up the dipstick 10 by capillary action. As the sample solution 14 passes the conjugate zone 26, it mobilises the anti-biotin antibody-dye conjugate 24. Released anti-biotin antibody-dye conjugate 24 can then bind to the biotin coupled to the detection probe 28 hybridised to the target nucleic acid 12.

Complex formed between the anti-biotin antibody-dye conjugate 24, the detection probe 28, the helper probe 30 and the target nucleic acid 12 then moves up the dipstick 10 to the capture zone 22 where the target nucleic acid of the complex can hybridise to the immobilised capture probe 20. The capture probe 20 is immobilised at the capture zone 22 in such a way that it cannot be mobilised by the sample solution 14 as it moves past the capture zone 22. Consequently, the complex bound to the capture probe remains in the capture zone and can be detected by the presence of the dye of the anti-biotin antibody-dye conjugate at the capture zone.

If there is no CT target nucleic acid in the sample solution, the detection probe 28 cannot be captured at the capture zone 22 and so no dye is visible at the capture zone. If there is CT target nucleic acid in the sample solution, but insufficient amounts of the target nucleic acid can be captured at the capture zone the presence of the target nucleic acid in the sample solution will not be detected.

The capture of target nucleic acid described above is referred to as direct probe capture in the examples below. In example 5 below two further capture formats were used—universal probe capture and antibody capture. Universal probe capture relies on capture of the target nucleic acid using a hook probe hybridised to a universal probe immobilised to the capture zone of the dipstick. The hook probe is capable of hybridising to the target nucleic acid. The method of capture is identical to direct probe capture except the capture probe is replaced by the universal and hook probes.

With antibody capture, an antibody is immobilised at the capture zone of the dipstick instead of the capture probe. The capture probe comprises a probe coupled to a ligand (such as DNP) which can be bound by the antibody and is added to the sample solution with the helper and detection probes. The capture probe hybridises to target nucleic acid when the sample solution is heated and then cooled in order to hybridise the helper and detection probes to the target nucleic acid.

The contact end of the dipstick is contacted with the sample solution after incubation of the capture, helper and detection probes in the sample solution. Complex containing the target nucleic acid, capture probe, helper probe and detection probe (bound by the anti-biotin antibody-dye conjugate) is then captured at the capture zone by the antibody immobilised at the capture zone. Presence of target nucleic acid in the sample solution is again detected by the presence of the anti-biotin antibody-dye conjugate at the capture zone. Thus, hybridisation of the capture probe to the target occurs in the sample solution rather than on the dipstick.

It has been found that the sensitivity of detection of target nucleic acid can be reduced if the distance between the region of the target nucleic acid to which the capture probe hybridises and the region to which the detection probe hybridises is less than 26 nucleotides. Thus, it is preferred that the distance between these regions is at least 26 nucleotides and preferably at least 200 nucleotides.

EXAMPLE 1

Experimental Setup

Capture format: direct probe capture (cp) Seq ID No 13 immobilised on dipstick;

Detection format: detection probe (dp) comprising nucleic acid of Seq ID No 14, 15, 16, or 17 coupled to biotin at $10^{12}$ copies, and an anti-biotin antibody-dye conjugate to detect the detection probe;

Target DNA: 872 bp DNA at $10^{11}$–$10^9$ copies.

Helper probes: HP SEQ ID No 1' (24 mer, G+C=9 nucleotides, Tm=72.2° C., which hybridises to a sequence of the target spaced 11 nucleotides from the 5'-end of the capture probe when hybridised to the target nucleic acid) or HP SEQ ID No 1 (24 mer, G+C=8 nucleotides, Tm=70.5° C., which hybridises to sequence of the target nucleic acid immediately adjacent the 5'-end of capture probe when hybridised to the target nucleic acid) at $10^{12}$ copies.

| | Results | | | |
| --- | --- | --- | --- | --- |
| Target copies | $10^{11}$ | $10^{10}$ | $5 \times 10^9$ | $10^9$ |
| Control (no helper) | 2.5 | 0.0 | 0.0 | 0.0 |
| HP SEQ ID No1' | 3.0 | 1.0 | 0.0 | 0.0 |
| HP SEQ ID No1 | 5.0 | 3.5 | 2.5 | 0.0 |

Conclusions

A helper probe improves the sensitivity of target nucleic acid detection by more than 10-fold.

HP SEQ ID NO:1, which hybridises to a sequence of the target nucleic acid immediately adjacent the 5'-end of the capture probe when this has hybridised to the target nucleic acid, has a stronger helper effect than HP SEQ ID NO:1, which hybridises to a sequence of the target nucleic acid which is spaced 11 nucleotides from the 5'-end of the capture probe when this has hybridised to the target nucleic acid. HP SEQ ID NO:1 has a 2° C. higher Tm than HP SEQ ID NO: 1'. However, the distance between the capture probe and the helper probe is thought to be more important than the Tm and G+C content.

EXAMPLE 2

Experimental Setup

Capture format: direct probe capture (cp) (Seq ID No 14) immobilised on dipstick;

Detection format: detection probe (dp) comprising nucleic acid of Seq ID No 13 coupled to biotin at $10^{12}$ copies, and an anti-biotin antibody-dye conjugate;

Target DNA: 416 bp DNA at $5 \times 10^{10}$ copies.

Helper probes: combinations of helper probe HP SEQ ID No1, HP SEQ ID No 2, HP SEQ ID No 3, Seq ID No 15, Seq ID No 16 and Seq ID No 17 at $10^{12}$ copies.

Figure 4:
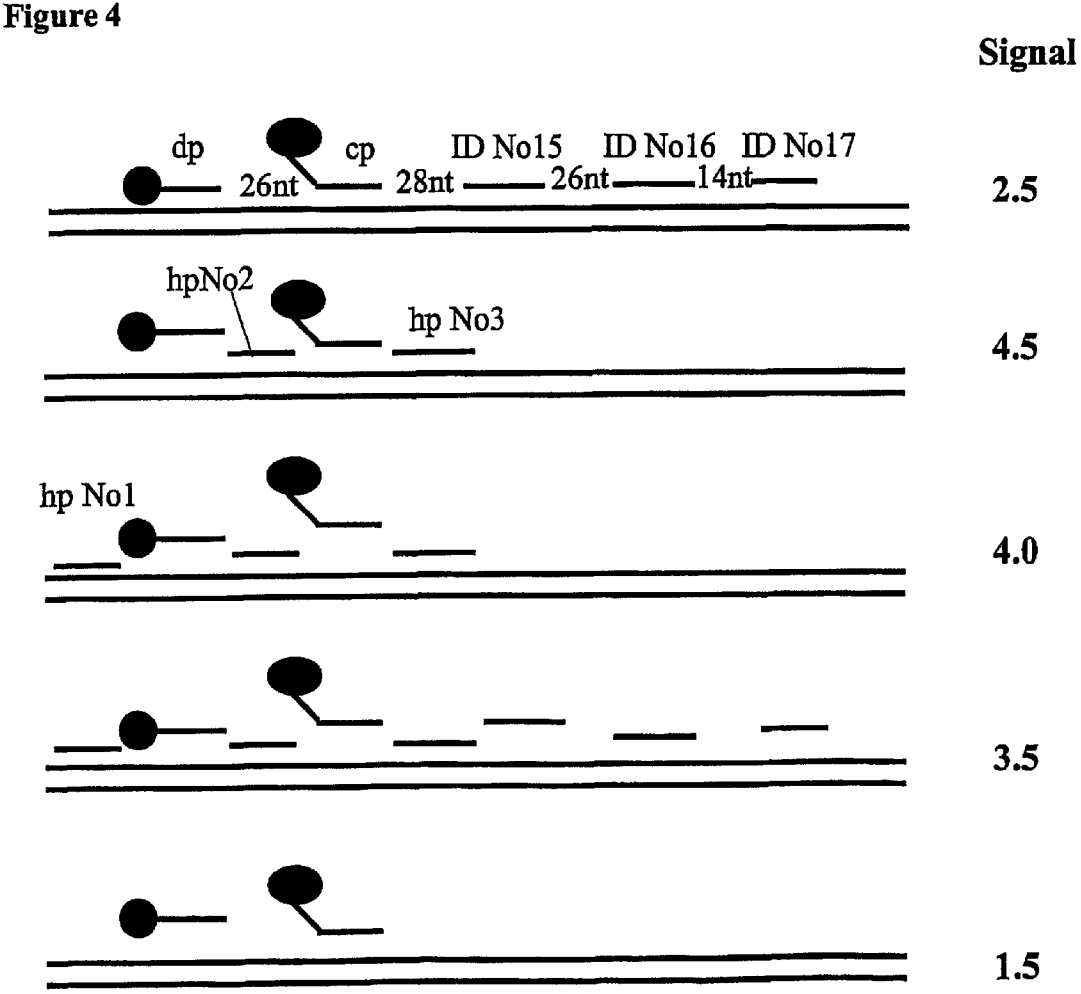
FIG. 4 shows the experimental set for Example 2.
Figure 5:
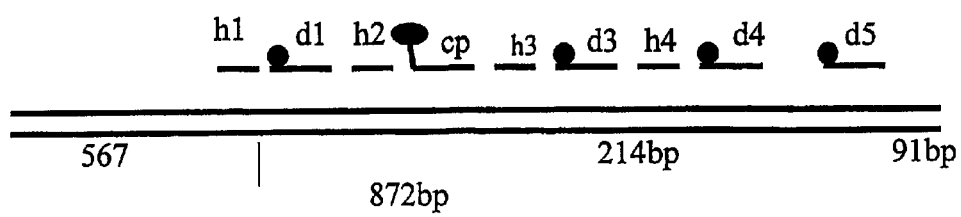
FIG. 5 shows the experimental set for Example 3.
Figure 6:
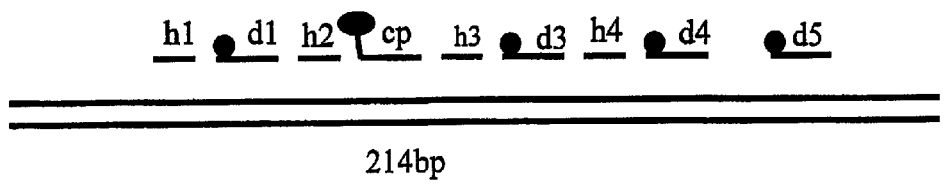
FIG. 6 shows the experimental set for Example 4.

Results
  See FIG. 4
Conclusions
  Helper probes which hybridise to a sequence of the target nucleic acid immediately adjacent the sequence recognized by the capture probe have the strongest enhancing effect on the sensitivity of detection of target nucleic acid in this example (compare signal 4.5 with 1.5 for control lacking helper probe).
  The effect on the sensitivity of detection of target nucleic acid by helper probes which hybridise to a sequence of the target nucleic acid immediately adjacent the sequence recognised by the capture probe is much stronger than the effect of helper probes which hybridise to sequences of the target nucleic acid distant from the sequence recognised by the capture probe (compare signal 4.5 with signal 2.5).

EXAMPLE 3

Experimental Set Up
  Capture format: direct probe capture (cp) Seq ID No 14 (immobilised on the dipstick);
  Detection format: detection probe comprising nucleic acid of
  Seq ID No 13 (d1), 15 (d3) 16 (d4) or 17 (d5) coupled to biotin at $10^{12}$ copies, and an anti-biotin antibody-dye conjugate;
  Target DNA: 872 bp DNA at $10^{10}$ copies.
  Helper probes: combinations of helper probes h1=HP SEQ ID No1, h2=HP SEQ ID No 2, h3=HP SEQ ID No 3, h4=HP SEQ ID No 4, at $10^{12}$ or $10^{13}$ copies.

| helper probe | Results at E12 copies | | | | | | at E13 copies |
|---|---|---|---|---|---|---|---|
| added | 0 | h2 + h3 | h2 | h3 | h1 + h2 + h3 | h1 + h2 + h3 + h4 | h1 + h2 + h3 + h4 |
| signal | 1.5 | 3.5 | 2.5 | 3 | 3.5 | 3.5 | 3.5 |

Conclusions
  Helper probes (h2 and h3) which hybridise to sequences of the target nucleic acid adjacent each side of the sequence recognised by the capture probe enhance the sensitivity of detection compared to the sensitivity of detection using only one of the helper probes.
  Increasing the concentration of helper probe ($10^{13}$ compared to $10^{12}$ copies) did not have any effect on the sensitivity of detection in this example.

EXAMPLE 4

Experimental Setup
  Capture format: direct probe capture (cp) Seq ID No 14 (immobilised on the dipstick);
  Detection format: detection probe comprising nucleic acid of Seq ID No 13 (d1), 15 (d3) 16 (d4) or 17 (d5) coupled to biotin at $10^{12}$ copies, anti-biotin antibody-dye conjugate;
  Helper probes: combinations of helper probe h1=HP SEQ ID No1, h2=HP SEQ ID No 2, h3=HP SEQ ID No 3, h4=HP SEQ ID No 4, at $10^{12}$ or $10^{13}$ copies;
  Targets: circular double stranded DNA plasmids pCTL15B (5.1 Kbp) and pCTL131(6.3 Kbp), plasmid pCTL130 lacking complementary sequences to the capture and detection probes to act as a negative control, and double stranded linear DNA (872 bp) at $10^{11}$ copies to act as a positive control.

| | Result | | |
|---|---|---|---|
| target | h2 + h3 | h1 + h2 + h3 + h4 | without hp |
| pCTL130 | 0.0 | 0.0 | 0.0 |
| pCTL131 | 1.5 | 1.5 | 0.0 |
| pCTL15B | 1.5 | 1.5 | 0.0 |
| 872 bp DNA | 5.0 | 5.0 | 3.5 |

Conclusion
  Circular double stranded DNA, longer than 5 Kbp, could be detected using helper probes which hybridise to sequence of the target nucleic adjacent the sequence recognised by the capture probe.
  Helper probes which hybridise to sequence of the target nucleic acid distant from the sequence recognised by the capture probe but adjacent the sequence recognised by the detection probe (helper probes h1 and h4) did not enhance the sensitivity of nucleic acid detection in this example. Under the conditions in this example the helper probes appear primarily to enhance hybridisation of the capture probe to the double stranded circular target nucleic acid on the dipstick.
  The sensitivity of detection of the circular double stranded DNA targets (5.1 Kbp or 6.3 Kbp) is lower than the sensitivity of detection of the linear double stranded 872 bp DNA. As the size of the target nucleic acid increases, the efficiency of hybridisation of the detection and capture probes to the target nucleic acid is expected to reduce. The accessibility of the detection probe to the anti-biotin antibody-dye conjugate is also thought to be reduced as the target size increases. Detection of double stranded target nucleic acid is thought to be less efficient than detection of single stranded target nucleic acid because the efficiency of hybridisation of the detection probe and the capture probe to the target nucleic acid decreases. The accessibility of the detection probe to the anti-biotin antibody-dye conjugate is also thought to be reduced for double stranded compared to single stranded target nucleic acid.

EXAMPLE 5

Experimental Setup
  Capture sequence: SEQ ID No 15
  Capture formats:
  i) direct probe capture—probe Seq ID No 15 immobilised on the dipstick;
  ii) universal probe capture—20 nucleotide universal probe immobilised on the dipstick hybridised to a hook probe with sequence complimentary to the sequence of the universal probe and to the target DNA sequence (SEQ ID No 15);
  iii) antibody capture—anti-DNP antibody immobilised on the dipstick, capture probe comprising nucleic acid of SEQ ID No 15 coupled to DNP and hybridised to the target nucleic acid in the sample solution;
  Detection format: detection probe comprising nucleic acid of Seq ID No 13, 14, 16 or 17 coupled to biotin at $10^{12}$ copies, anti-biotin antibody-dye conjugate;

Helper probes: HP SEQ ID No 3 and HP SEQ ID No 4, at $10^{12}$ copies;

Target: 872 bp DNA at $10^{11}$ to $10^8$ copies.

Results

Figure 7:
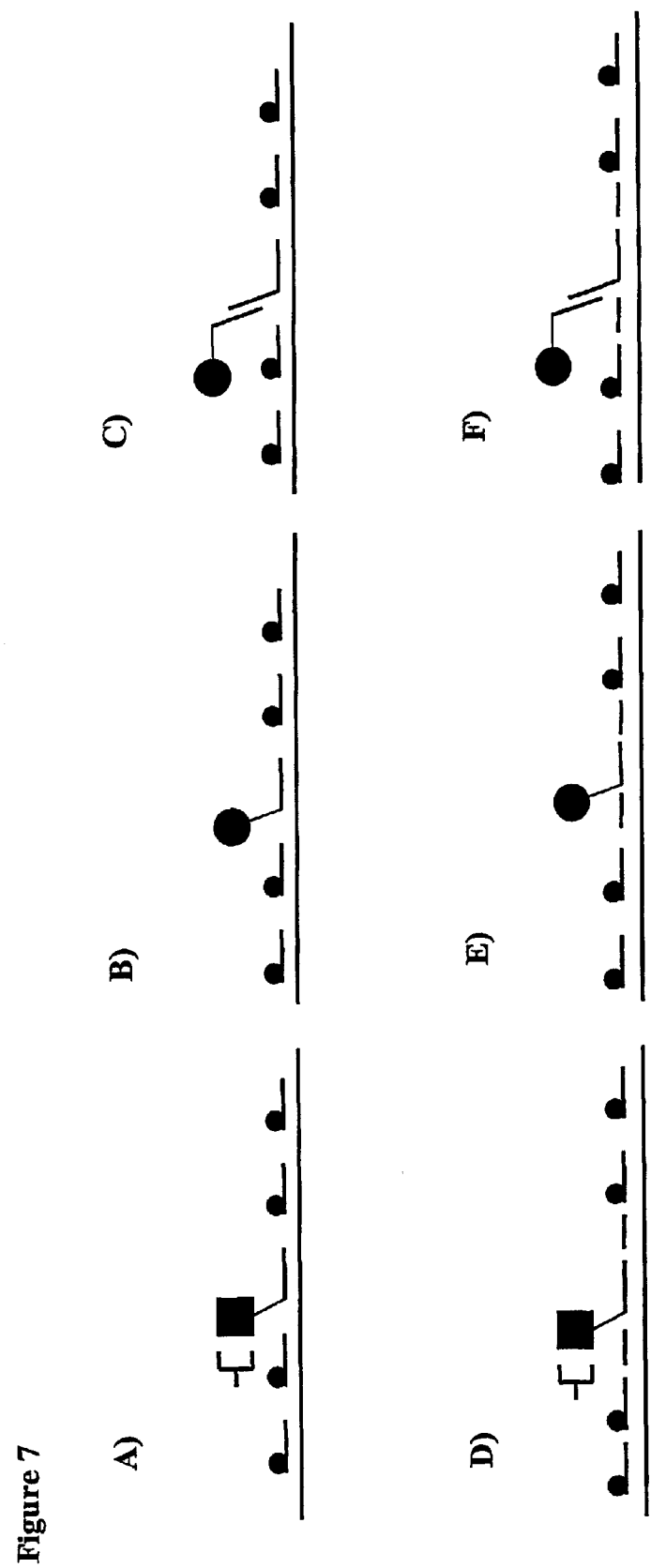
FIG. 7 shows the experimental setup for Example 5, and figure legends are shown in FIG. 11.

See FIG. 7;

Conclusion

The helper probes improved the sensitivity of detection of target nucleic acid using direct probe capture (see (i) above) and universal probe capture (see (ii) above). These results support the conclusions of examples 2, 3 and 4 that helper probes enhance hybridisation between nucleic acids on the dipstick.

EXAMPLE 6

Experimental Setup

Capture format: Direct probe capture (cp) (SEQ ID No 10) immobilised on the dipstick;

Detection format: detection probe (dp) comprising nucleic acid of Seq ID No 13 coupled to biotin at $10^{12}$ copies, anti-biotin antibody-dye conjugate;

Helper probes: HP SEQ ID No 5 and HP SEQ ID No 6 which hybridise to a sequence of the target nucleic acid adjacent the sequence recognised by SEQ ID No 10; HP SEQ ID No 1 and HP SEQ ID No 2 which hybridise to sequence of the target nucleic acid adjacent the sequence recognised by SEQ ID No 13 at $10^{12}$ copies;

Target: 872 bp DNA at $5\times10^{10}$ copies.

Results

Figure 8:
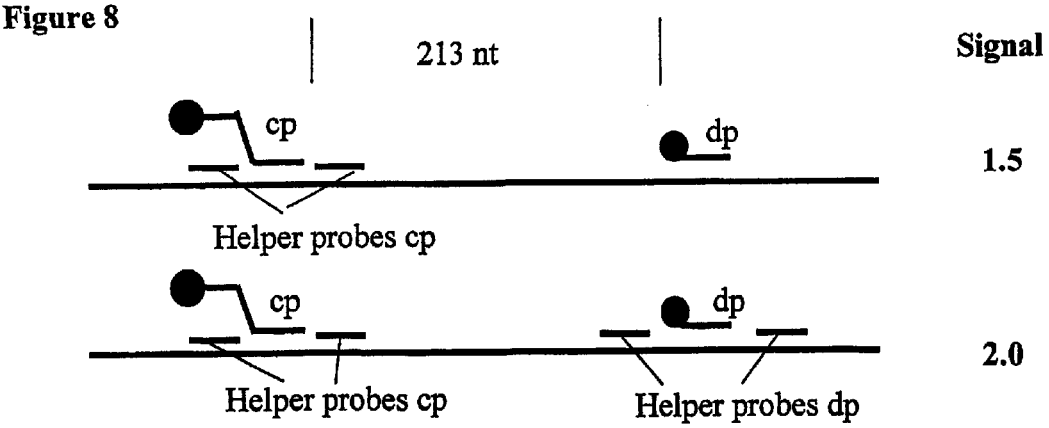
FIG. 8 shows the experimental set for Example 6.

See FIG. 8.

Conclusion

When the capture probe and detection probe hybridise to sequences of the target nucleic acid which are more than 200 nt apart, the sensitivity of detection of target nucleic acid was improved with helper probes that hybridise to sequence of the target nucleic acid adjacent each side of the sequence recognised by the detection probe.

EXAMPLE 7

Effect of Helper Probes on CT Detection

Experimental Setup

Capture sequence: SEQ ID No 15

Capture formats:

Direct probe capture: probe comprising nucleic acid of Seq ID No 15 coupled to BSA immobilised to the dipstick membrane;

Antibody capture: Anti-DNP antibody (α-DNP capture) immobilised to the dipstick membrane; capture probe comprising nucleic acid of SEQ ID No 15 coupled to DNP.

Detection format: detection probe comprising nucleic acid of Seq ID No 18 or 13 each coupled to several biotin detection ligands, and an anti-biotin antibody—dye conjugate. $10^{12}$ copies of the detection probes;

Helper probes: HP SEQ ID No 3 and HP SEQ ID No 4, at $10^{12}$ copies. The helper probes are capable of hybridising adjacent the region of the target nucleic acid recognised by the capture probe;

Target: CT Elementary Bodies's at $2.4 \cdot 10^7$ copies/test.

| | Results | | | |
|---|---|---|---|---|
| | Capture: | | | |
| | Direct Probe Capture | | Ab Capture | |
| Helpers | Yes | No | Yes | No |
| Signal | 4.0 | 2.5 | 1.5 | 0.5 |

Conclusions from Example 7

Detection of the cryptic plasmid of CT cells using direct probe capture or antibody capture was improved by the use of helper probes.

Use of helper probes in accordance with the invention appears to enhance hybridisation occurring on the dipstick membrane or in solution.

In examples 1 to 7 above, the helper probes hybridise to the same strand of the double stranded target nucleic acid as the capture and detection probes. No enhancement of the sensitivity of detection of target nucleic acid was observed in similar experiments in which the helper probes hybridised to the opposite strand of the double stranded target nucleic acid to the strand recognised by the capture and detection probes.

EXAMPLE 8

One-tep Nucleic Acid Dipstick Assay Detection of *Chlamydia trachomatis*

Experimental Set-up:

Reagents:

Capture format: oligonucleotide probe capture immobilised on dipstick membrane via BSA carrier;

Detection format: multiple biotin labelled detector probe; anti-biotin antibody—colloidal gold conjugate;

Sample preparation: *Chlamydia trachomatis* (Ct) elementary bodies (EB) celles were prepared in ceoncentrations from $10^6$ copies/µl to $10^3$ copies/µl in PBS buffer and heated at $100°$ C. for 20 minutes;

Hybridisation/dipstick running buffer: Standard is hybridisation buffer comprising salt, detergent and a blocking protein such as BSA or powdered milk.

Method:

The detection probe, helper probe and $5\times10^6$–$5\times10^3$ copies of EB diluted in hybridisation buffer made up to 80 µl and heated at $100°$ C. for 7 minutes. The mixture was then centrifuged briefly to collect all the liquid and mixed with 20 µl anti-biotin Ab colloidal gold. The whole 100 µl mixture were wicked up on dipstick and let to develop a signal.

Results and Discussion

Figure 9:
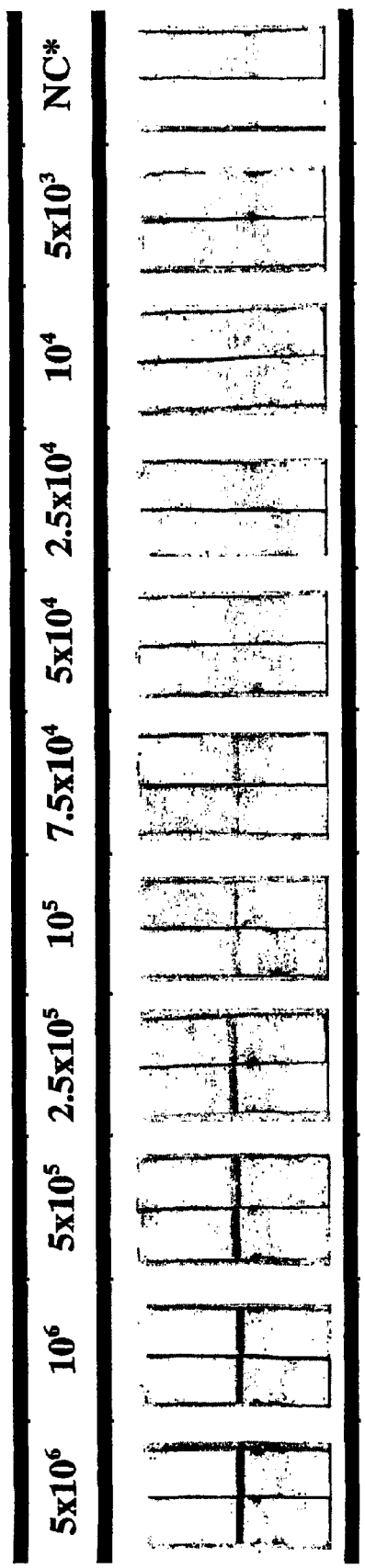
FIG. 9 shows the results of a one-step hybridization assay, which depicts one-step nucleic acid dipstick assay detection of *Clamydia trachomatis*. The numbers indicate the number of elementary bodies of *Clamydia trachomatis*. *NC=Negative Control.
Figure 11:
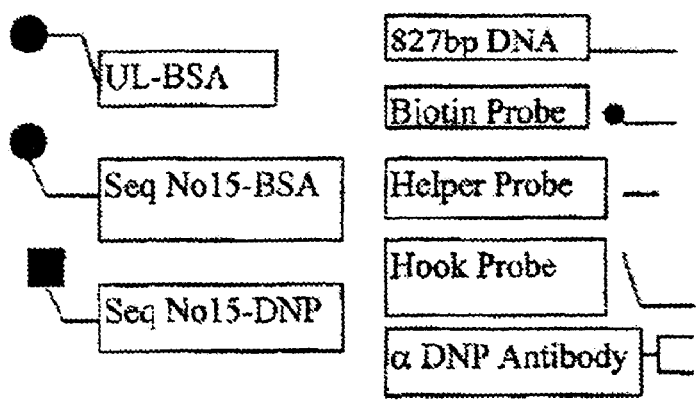
FIG. 11 shows figure legends for FIG. 7.

The results presented in the Table below and FIG. 9 (see the attached power point document) show that about $10^4$ copies of Ct EB could be detected with one step nucleic acid dipstick assay in less than an hour including the sample preparation step.

Although the so presented dipstick detection assay has a sensitivity of detection about equal to other sandwich hybridisation assays it has the major advantages of speed and simplicity.

A sandwich hybridisaiton assay for detection of Ct disclosed in PCT WO 93/1322 for example, is a complex multi-component microtitre plate format assay, which could not be accomplished for less than 5 hours. This assay is a multi-step assay, which requires a gradual addition of its components in a defined order with incubations and washing steps after the addition of every new component.

The nucleic acid dipstick assay subject of this invention could be done in one step with no need of different steps for addition of components and washings. This sandwich hybridisation assay does not require more than one solution conditions in order to render them advantageous for hybridisation and other affinity pair formations. The same solution conditions could serve a free migration of the components through the dipstick membrane as well.

Methods of the invention have been found to significantly enhance the sensitivity of detection of target nucleic acids by dipsticks. In particular, detection of double stranded nucleic acid and circular double stranded target nucleic acid is greatly improved.

The invention claimed is:

1. A dipstick assay method for testing for the presence of a target nucleic acid in a sample solution, wherein the method comprises:

contacting the sample solution with a dipstick to cause sample solution to move by capillary action to a capture zone of the dipstick thereby allowing target nucleic acid in the sample solution to be captured and detected at the capture zone; wherein:

a) a capture probe capable of hybridizing to the target nucleic acid is used to capture target nucleic acid at the capture zone, and hybridization of the capture probe to the target nucleic acid is enhanced by a helper probe that hybridizes to a different region of the target nucleic acid than the capture probe, or b) a detection probe capable of hybridizing to the target nucleic acid is used to detect target nucleic acid at the capture zone, and hybridization of the detection probe to the target nucleic is enhanced by a helper probe that hybridizes to a different region of the target nucleic acid than the detection probe.

2. A method according to claim 1, wherein the method comprises:

a) providing a chromatographic strip having a contact end for contacting the sample solution, and a capture probe that is immobilized at a capture zone of the chromatographic strip remote from the contact end, wherein the capture probe is capable of hybridizing to a first sequence of the target nucleic acid;

b) incubating the sample solution with:

a detection probe capable of attaching to the target nucleic acid under conditions for attachment of the detection probe to target nucleic acid, thereby allowing direct or indirect detection of target nucleic acid utilizing the detection probe, and a first helper probe capable of hybridizing to a second sequence of the target nucleic acid and thereby enhancing hybridization of the capture probe to target nucleic acid, wherein the sample solution and the first helper probe are incubated under conditions for hybridization of the first helper probe to the second sequence;

c) contacting the contact end of the chromatographic strip with the sample solution so that a complex formed between the detection probe, the first helper probe and target nucleic acid can move by capillary action to the capture zone and bind to the capture zone by hybridization of the capture probe to the target nucleic acid of the complex; and d) checking for the presence of the detection probe at the capture zone.

3. A method according to claim 1, wherein the method comprises:

a) providing a chromatographic strip having a contact end for contacting the sample solution, and a capture moiety immobilized at a capture zone of the chromatographic strip remote from the contact end;

b) incubating the sample solution with:

a detection probe capable of attaching to the target nucleic acid under conditions for attachment of the detection probe to target nucleic acid, thereby allowing direct or indirect detection of target nucleic acid utilizing the detection probe, a capture probe capable of hybridizing to a first sequence of the target nucleic acid under conditions for hybridization of the capture probe to the first sequence, wherein the capture probe is capable of binding the capture moiety when the capture probe is hybridized to the first sequence, and a first helper probe capable of hybridizing to a second sequence of the target nucleic acid and thereby enhancing hybridization of the capture probe to target nucleic acid, wherein the sample solution and the first helper probe are incubated under conditions for hybridization of the first helper probe to the second sequence;

c) contacting the contact end of the chromatographic strip with the sample solution so that a complex formed between the detection probe, the capture probe, the first helper probe and target nucleic acid can move by capillary action to the capture zone and bind to the capture zone by binding of the capture moiety to the capture probe of the complex; and d) checking for the presence of the detection probe at the capture zone.

4. The method according to claim 2, wherein the second sequence is spaced up to 10 nucleotides from the first sequence.

5. The method according to claim 4, wherein the second sequence is immediately adjacent to the first sequence.

6. The method according to claim 2, wherein the sample solution is incubated with a second helper probe capable of hybridizing to a third sequence of the target nucleic acid and thereby enhancing hybridization of the capture probe to target nucleic acid, wherein the sample solution and the second helper probe are incubated under conditions for hybridization of the second helper probe to the third sequence.

7. The method according to claim 6, wherein the second and third sequences flank the first sequence.

8. The method according to claim 7, wherein the third sequence is spaced up to 10 nucleotides from the first sequence.

9. The method according to claim 8, wherein the third sequence is immediately adjacent to the first sequence.

10. The method according to claim 2, wherein the detection probe comprises a hook detection probe capable of hybridizing to the target nucleic acid; and a universal detection probe capable of hybridizing to the hook detection probe.

11. The method according to claim 2, wherein the detection probe is capable of hybridizing to a fourth sequence of the target nucleic acid to attach the detection probe to the target nucleic acid.

12. The method according to claim 11, wherein the sample solution is incubated with a third helper probe capable of hybridizing to a fifth sequence of the target nucleic acid, thereby enhancing hybridization of the detection probe to the fourth sequence, wherein the third helper probe and the sample solution are incubated under conditions for hybridization of the third helper probe to the fifth sequence.

13. A method for testing according to claim 1, wherein the method comprises:

a) providing a chromatographic strip having a contact end is for contacting the sample solution, and a capture probe immobilized at a capture zone of the chromatographic strip remote from the contact end, wherein the capture probe is capable of hybridizing to the target nucleic acid;

b) contacting the sample solution with a helper probe capable of hybridizing to the target nucleic acid and thereby enhancing hybridization of the capture probe to the target nucleic acid, wherein the sample solution is contacted with the helper probe under conditions for hybridization of the helper probe to the target nucleic acid;

c) contacting the contact end of the chromatographic strip with the sample solution to cause sample solution to move by capillary action to the capture zone so that a complex formed between the helper probe and the target nucleic acid can be captured at the capture zone by hybridization of the capture probe to the target nucleic acid of the complex; and d) checking for the presence of the target nucleic acid at the capture zone.

14. A method according to claim 1, wherein the method comprises:

a) providing a chromatographic strip having a contact end for contacting the sample solution, and a capture moiety immobilized at a capture zone of the chromatographic strip remote from the contact end;

b) contacting the sample solution with:

a capture probe capable of hybridizing to the target nucleic acid under conditions for hybridization of the capture probe to the target nucleic acid, wherein the capture probe is capable of binding the capture moiety when the capture probe is hybridized to the target nucleic acid, and a helper probe capable of hybridizing to the target nucleic acid and thereby enhancing hybridization of the capture probe to the target nucleic acid, wherein the sample solution and the helper probe is contacted under conditions for hybridization of the helper probe to the target nucleic acid;

c) contacting the contact end of the chromatographic strip with the sample solution to cause sample solution to move by capillary action to the capture zone so that a complex formed between the capture probe, the helper probe, and the target nucleic acid can be captured at the capture zone by binding of the capture moiety to the capture probe of the complex; and d) checking for the presence of target nucleic acid at the capture zone.

15. The method according to claim 2, wherein the capture probe comprises a universal capture probe hybridized to a hook capture probe.

16. A method according to claim 1, wherein the method comprises:

a) providing a chromatographic strip having a contact end for contacting the sample solution, and a capture probe immobilized at a capture zone of the chromatographic strip remote from the contact end, wherein the capture probe is capable of hybridizing to a first sequence of the target nucleic acid;

b) incubating the sample solution with:

a detection probe capable of hybridizing to a second sequence of the target nucleic acid under conditions for hybridization of the detection probe to target nucleic acid, thereby allowing direct or indirect detection of the target nucleic acid utilizing the detection probe, and a first helper probe capable of hybridizing to a third sequence of the target nucleic acid and thereby enhancing hybridization of the detection probe to the second sequence, wherein the sample solution and the first helper probe are incubated under conditions for hybridization of the first helper probe to the third sequence:

c) contacting the contact end of the chromatographic strip with the sample solution so that a complex formed between the detection probe, the first helper probe, and the target nucleic acid can move by capillary action to the capture zone and bind to the capture zone by hybridization of the capture probe to the target nucleic acid of the complex; and d) checking for the presence of the detection probe at the capture zone.

17. A method according to claim 1, wherein the method comprises:

a) providing a chromatographic strip having a contact end for contacting the sample solution, and a capture moiety immobilized at a capture zone of the chromatographic strip remote from the contact end;

b) incubating the sample solution with:
a capture probe capable of hybridizing to a first sequence of the target nucleic acid under conditions for hybridization of the capture probe to the first sequence, wherein the capture probe is capable of binding the capture moiety when the capture probe is hybridized to the first sequence,
a detection probe capable of hybridizing to a second sequence of the target nucleic acid under conditions for hybridization of the detection probe to the second sequence, thereby allowing direct or indirect detection of target nucleic acid utilizing the detection probe, and
a first helper probe capable of hybridizing to a third sequence of the target nucleic acid and thereby enhancing hybridization of the detection probe to target nucleic acid, wherein the sample solution and the first helper probe are incubated under conditions for hybridization of the first helper probe to the third sequence;
c) contacting the contact end of the chromatographic strip with the sample solution so that a complex formed between the detection probe, the capture probe, the first helper probe, and the target nucleic acid can move by capillary action to the capture zone and bind to the capture zone by binding of the capture moiety to the capture probe of the complex; and
d) checking for the presence of detection probe at the capture zone.

18. The method according to claim 16, wherein the third sequence is spaced up to 10 nucleotides from the second sequence.

19. The method according to claim 18, wherein the third sequence is immediately adjacent to the second sequence.

20. The method according to claim 16, wherein the sample solution is incubated with a second helper probe capable of hybridizing to a fourth sequence of the target nucleic acid and thereby enhancing hybridization of the detection probe to target nucleic acid, wherein the sample solution and the second helper probe are incubated under conditions for hybridization of the second helper probe to the fourth sequence.

21. The method according to claim 20, wherein the third and fourth sequences flank the second sequence.

22. The method according to claim 21, wherein the fourth sequence is spaced up to 10 nucleotides from the second sequence.

23. The method according to claim 22, wherein the fourth sequence is immediately adjacent to the second sequence.

24. The method according to claim 16, wherein the capture probe comprises a universal capture probe hybridized to a hook capture probe.

25. The method according to claim 2, wherein hybridization of the probes to target nucleic acid in the sample solution is carried out in a single step.

26. A method according to claim 1, wherein the method comprises:
a) providing a chromatographic strip having a contact end for contacting the sample solution, a capture probes immobilized at a capture zone of the chromatographic strip remote from the contact end, wherein the capture probe is capable of hybridizing to the target nucleic acid, and a helper probe releasably immobilized to the chromatographic strip between the contact end and the capture zone, wherein the helper probe is capable of hybridizing to the target nucleic acid and thereby enhancing hybridization of the capture probe to the target nucleic acid;
b) contacting the contact end of the chromatographic strip with the sample solution to cause sample solution to move by capillary action to the capture zone, thereby releasing helper probe from the chromatographic strip and allowing released helper probe to hybridize to target nucleic acid in the sample solution as it travels to the capture zone, so that a complex comprising target nucleic acid and helper probe can be captured at the capture zone by hybridization of the capture probe to the target nucleic acid of the complex; and
c) checking for the presence of the target nucleic acid at the capture zone.

27. A method according to claim 1, wherein the method comprises:
a) providing a chromatographic strip having a contact end for contacting the sample solution, a capture moiety immobilized at a capture zone of the chromatographic strip remote from the contact end, and a capture probe releasably immobilized to the chromatographic strip between the contact end and the capture zone, wherein the capture probe is capable of hybridizing to the target nucleic acid and capable of binding the capture moiety when the capture probe is hybridized to the target nucleic acid;
b) incubating the sample solution with:
a helper probe capable of hybridizing to the target nucleic acid and thereby enhancing hybridization of the capture probe to target nucleic acid, under conditions for hybridization of the helper probe to the target nucleic acid; and
c) contacting the contact end of the chromatographic strip with the sample solution to cause sample solution to move by capillary action to the capture zone, thereby releasing capture probe from the chromatographic strip so that released capture probe can hybridize to target nucleic acid in the sample solution as it travels to the capture zone, and so that a complex comprising target nucleic acid, capture probe and helper probe can be captured at the capture zone by binding of the capture moiety to the capture probe of the complex; and
d) checking for the presence of target nucleic acid at the capture zone.

28. A method according to claim 1, wherein the method comprises:
a) providing a chromatographic strip having a contact end for contacting the sample solution, a capture moiety immobilized at a capture zone of the chromatographic strip remote from the contact end, a capture probe releasably immobilized to the chromatographic strip between the contact end and the capture zone, wherein the capture probe is capable of hybridizing to the target nucleic acid and capable of binding the capture moiety when the capture probe is hybridized to the target nucleic acid, and a helper probe releasably immobilized to the chromatographic strip between the contact end and the capture zone, wherein the helper probe is capable of hybridizing to the target nucleic acid and thereby enhancing hybridization of the capture probe to the target nucleic acid; and
b) contacting the contact end of the chromatographic strip with the sample solution to cause sample solution to move by capillary action to the capture zone, thereby releasing the capture probe and the helper probe from the chromatographic strip so that released the capture probe and the helper probe can hybridize to the target nucleic acid in the sample solution as it travels to the capture zone, and so that a complex comprising the target nucleic acid, the capture probe and the helper probe can be captured at the capture zone by binding of the capture moiety to the capture probe of the complex; and c) checking for the presence of the target nucleic acid at the capture zone.

29. A method according to claim 1, wherein the method comprises:
   a) providing a chromatographic strip having a contact end for contacting the sample solution, a capture probe immobilized at a capture zone of the chromatographic strip remote from the contact end, wherein the capture probe is capable of hybridizing to the target nucleic acid, and a detection probe releasably immobilized to the chromatographic strip between the contact end and the capture zone, wherein the detection probe is capable of hybridizing to the target nucleic acid and thereby allowing direct or indirect detection of the target nucleic acid utilizing the detection probe;
   b) incubating the sample solution with:
   a helper probe capable of hybridizing to the target nucleic acid and thereby enhancing hybridization of the detection probe to the target nucleic acid, wherein the sample solution and the helper probe are incubated under conditions for hybridization of the helper probe to the target nucleic acid;
   c) contacting the contact end of the chromatographic strip with the sample solution to cause the sample solution to move by capillary action to the capture zone, thereby releasing the detection probe from the chromatographic strip so that released the detection probe can hybridize to the target nucleic acid in the sample solution as it travels to the capture zone, and so that a complex comprising the target nucleic acid, the helper probe, and the detection probe can be captured at the capture zone by hybridization of the capture probe to the target nucleic acid of the complex; and
   d) checking for the presence of the detection probe at the capture zone.

30. A method according to claim 1, wherein the method comprises:
   a) providing a chromatographic strip having a contact end for contacting the sample solution, a capture probe immobilized at a capture zone of the chromatographic strip remote from the contact end, wherein the capture probe is capable of hybridizing to the target nucleic acid, a detection probe releasably immobilized to the chromatographic strip between the contact end and the capture zone, wherein the detection probe is capable of hybridizing to the target nucleic acid and thereby allowing direct or indirect detection of target nucleic acid utilizing the detection probe, and a helper probe releasably immobilized to the chromatographic strip between the contact end and the capture zone, wherein the helper probe is capable of hybridizing to the target nucleic acid and thereby enhancing hybridization of the detection probe to the target nucleic acid; and
   b) contacting the contact end of the chromatographic strip with the sample solution to cause sample solution to move by capillary action to the capture zone, thereby releasing the helper probe and the detection probe from the chromatographic strip so that released the helper probe and the detection probe can hybridize to target nucleic acid in the sample solution as it travels to the capture zone, and so that a complex comprising the target nucleic acid, the helper probe, and the detection probe can be captured at the capture zone by hybridization of the capture probe to the target nucleic acid of the complex; and
   c) checking for the presence of the detection probe at the capture zone.

31. A method according to claim 1, wherein the method comprises:
   a) providing a chromatographic strip having: a contact end for contacting the sample solution, a capture moiety immobilized at a capture zone of the chromatographic strip remote from the contact end, and a capture probe releasably immobilized to the chromatographic strip between the contact end and the capture zone, wherein the capture probe is capable of hybridizing to the target nucleic acid and is capable of binding the capture moiety when the capture probe is hybridized to the target nucleic acid;
   b) incubating the sample solution with:
   a detection probe capable of hybridizing to the target nucleic acid thereby allowing direct or indirect detection of target nucleic acid utilizing the detection probe, wherein the detection probe is incubated with the sample solution under conditions for hybridization of the detection probe to the target nucleic acid, and a helper probe capable of hybridizing to the target nucleic acid and thereby enhancing hybridization of the detection probe to the target nucleic acid, wherein the sample solution and the helper probe are incubated under conditions for hybridization of the helper probe to the target nucleic acid;
   c) contacting the contact end of the chromatographic strip with the sample solution to cause sample solution to move by capillary action to the capture zone thereby releasing the capture probe from the chromatographic strip so that the released capture probe can hybridize to the target nucleic acid in the sample solution as it travels to the capture zone, and so that a complex comprising the target nucleic acid, the capture probe, the helper probe, and the detection probe can be captured at the capture zone by binding of the capture moiety to the capture probe of the complex; and
   d) checking for the presence of the detection probe at the capture zone.

32. A method according to claim 1, wherein the method comprises:
   a) providing a chromatographic strip having a contact end for contacting the sample solution, a capture moiety immobilized at a capture zone of the chromatographic strip remote from the contact end, and a detection probe releasably immobilized to the chromatographic strip between the contact end and the capture zone, wherein the detection probe is capable of hybridizing to the target nucleic acid thereby allowing direct or indirect detection of the target nucleic acid utilizing the detection probe;
   b) incubating the sample solution with:
   a capture probe capable of hybridizing to the target nucleic acid and capable of binding the capture moiety when the capture probe is hybridized to the target nucleic acid, under conditions for hybridization of the capture probe to the target nucleic acid, and
   a helper probe capable of hybridizing to the target nucleic acid and thereby enhancing hybridization of the detection probe to the target nucleic acid, under conditions for hybridization of the helper probe to the target nucleic acid;

c) contacting the contact end of the chromatographic strip with the sample solution to cause sample solution to move by capillary action to the capture zone, thereby releasing the detection probe from the chromatographic strip so that the released detection probe can hybridize to the target nucleic acid in the sample solution as it travels to the capture zone, and so that a complex comprising the target nucleic acid, the capture probe, the helper probe, and the detection probe can be captured at the capture zone by binding of the capture moiety to the capture probe of the complex; and d) checking for the presence of the detection probe at the capture zone.

33. A method according to claim 1, wherein the method comprises:

a) providing a chromatographic strip having a contact end for contacting the sample solution, a capture moiety immobilized at a capture zone of the chromatographic strip remote from the contact end, a detection probe releasably immobilized to the chromatographic strip between the contact end and the capture zone, wherein the detection probe is capable of hybridizing to the target nucleic acid thereby allowing direct or indirect detection of target nucleic acid utilizing the detection probe, and a helper probe releasably immobilized to the chromatographic strip, wherein the helper probe is capable of hybridizing to the target nucleic acid and thereby enhancing hybridization of the detection probe to the target nucleic acid;

b) incubating the sample solution with:
a capture probe capable of hybridizing to the target nucleic acid and capable of binding the capture moiety when the capture probe is hybridized to the target nucleic acid, wherein the capture probe is incubated with the sample solution under conditions for hybridization of the capture probe to the target nucleic acid, and a helper probe capable of hybridizing to the target nucleic acid and thereby enhancing hybridization of the detection is probe to the target nucleic acid, wherein the helper probe is incubated with the sample solution under conditions for hybridization of the helper probe to the target nucleic acid;

c) contacting the contact end of the chromatographic strip with the sample solution to cause the sample solution to move by capillary action to the capture zone, thereby releasing the detection probe and the helper probe from the chromatographic strip so that the released detection probe and the helper probe can hybridize to the target nucleic acid in the sample solution as it travels to the capture zone, and so that a complex comprising the target nucleic acid, the capture probe, the helper probe, and the detection probe can be captured at the capture zone by binding of the capture moiety to the capture probe of the complex; and d) checking for the presence of the detection probe at the capture zone.

34. A method according to claim 1, wherein the method comprises:

a) providing a chromatographic strip having a contact end for contacting the sample solution, a capture moiety immobilized at a capture zone of the chromatographic strip remote from the contact end, a detection probe releasably immobilized to the chromatographic strip between the contact end and the capture zone, wherein the detection probe is capable of hybridizing to the target nucleic acid thereby allowing direct or indirect detection of target nucleic acid utilizing the detection probe, and a capture probe releasably immobilized to the chromatographic strip between the contact end and the capture zone, wherein the capture probe is capable of hybridizing to the target nucleic acid and capable of binding the capture moiety when the capture probe is hybridized to the target nucleic acid;

b) incubating the sample solution with a helper probe capable of hybridizing to the target nucleic acid and thereby enhancing hybridization of the detection probe to target nucleic acid, wherein the helper probe is incubated with the sample solution under conditions for hybridization of the helper probe to the target nucleic acid;

c) contacting the contact end of the chromatographic strip with the sample solution to cause the sample solution to move by capillary action to the capture zone, thereby releasing the detection probe and the capture probe from the chromatographic strip so that the released detection probe and the released capture probe can hybridize to target nucleic acid in the sample solution as lit travels to the capture zone, and so that a complex comprising the target nucleic acid, the capture probe, the helper probe and the detection probe can be captured at the capture zone by binding of the capture moiety to the capture probe of the complex; and d) checking for the presence of the detection probe at the capture zone.

35. A method according to claim 1, wherein the method comprises:

a) providing a chromatographic strip having a contact end for contacting the sample solution, a capture moiety immobilized at a capture zone of the chromatographic strip remote from the contact end, a detection probe releasably immobilized to the chromatographic strip between the contact end and the capture zone, wherein the detection probe is capable of hybridizing to the target nucleic acid thereby allowing direct or indirect detection of target nucleic acid utilizing the detection probe, a helper probe releasably immobilized to the chromatographic strip between the contact is end and the capture zone, wherein the helper probe is capable of hybridizing to the target nucleic acid and thereby enhancing hybridization of the detection probe to the target nucleic acid, and a capture probe releasably immobilized to the chromatographic strip between the contact end and the capture zone, wherein the capture probe is capable of hybridizing to the target nucleic acid and capable of binding the capture moiety when the capture probe is hybridized to the target nucleic acid;

b) contacting the contact end of the chromatographic strip with the sample solution to cause the sample solution to move by capillary action to the capture zone, thereby releasing the detection probe, the helper probe and the capture probe from the chromatographic strip so that the released detection probe, the helper probe and the capture probe can hybridize to the target nucleic acid in the sample solution as it travels to the capture zone, and so that a complex comprising the target nucleic acid, the capture probe, the helper probe, and the detection probe can be captured at the capture zone by binding of the capture moiety to the capture probe of the complex; and c) checking for the presence of the detection probe at the capture zone.

* * * * *

```
                        SEQUENCE LISTING

<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gataaaatcc ctttacccat gaaa                                            24

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taaaatgtcc tgattagtga aataat                                          26

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcggtatttt tttatataaa catgaaaa                                        28

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tgcaagatat cgagtatgcg ttgtta                                          26

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
aaagggaaaa ctcttgcaga                                              20

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcttttctaa agacaaaaaa gatcctcgat                                   30

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cttgctgctc gaacttgttt agtac                                        25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agaagtcttg gcagaggaaa ctttt                                        25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctagaattag attatgattt aaaaggg                                      27

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttcatatcca aggacaatag accaa                                        25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
```
tgatctacaa gtatgtttgt tgagt                                              25

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgcataataa cttcgaataa ggagaag                                            27

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tccctcgtga tataacctat ccg                                                23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
caggttgtta acaggatagc acgc                                               24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctcgttccga aatagaaaat cgca                                               24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggtaaagctc tgatatttga agac                                               24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

-continued

```
ctgaggcagc ttgctaatta tgagt                                          25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gttgggaaaa atagacatgg atcgg                                          25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cttgctgcaa agataaaatc cctt                                           24
```